United States Patent
Kamousi et al.

(10) Patent No.: US 10,743,809 B1
(45) Date of Patent: Aug. 18, 2020

(54) SYSTEMS AND METHODS FOR SEIZURE PREDICTION AND DETECTION

(71) Applicant: CeriBell, Inc., Mountain View, CA (US)

(72) Inventors: Baharan Kamousi, Redwood City, CA (US); Mehdi Hajinoroozi, Santa Clara, CA (US); Suganya Karunakaran, Sunnyvale, CA (US); Alexander Grant, Redwood City, CA (US); Jianchun Yi, San Jose, CA (US); Raymond Woo, Los Altos, CA (US); Josef Parvizi, Palo Alto, CA (US); Xingjuan Chao, Palo Alto, CA (US)

(73) Assignee: CeriBell, Inc., Mountain View, CA (US)

( * ) Notice: Subject to any disclaimer, the term of this patent is extended or adjusted under 35 U.S.C. 154(b) by 0 days.

(21) Appl. No.: 16/578,032

(22) Filed: Sep. 20, 2019

(51) Int. Cl.
| | |
|---|---|
| *A61B 5/00* | (2006.01) |
| *A61B 5/0476* | (2006.01) |
| *G06F 9/54* | (2006.01) |
| *G06N 20/00* | (2019.01) |

(52) U.S. Cl.
CPC .......... *A61B 5/4094* (2013.01); *A61B 5/0476* (2013.01); *A61B 5/7225* (2013.01); *A61B 5/7267* (2013.01); *G06F 9/542* (2013.01); *G06N 20/00* (2019.01)

(58) Field of Classification Search
None
See application file for complete search history.

(56) References Cited

U.S. PATENT DOCUMENTS

| | | | |
|---|---|---|---|
| 5,241,967 | A | 9/1993 | Yasushi et al. |
| 5,311,876 | A | 5/1994 | Olsen et al. |
| 6,735,467 | B2 | 5/2004 | Wilson |
| 9,173,610 | B2 | 11/2015 | Navakatikyan |

(Continued)

OTHER PUBLICATIONS

Abeg Kumar Jaiswal, et al. Epileptic Seizure Detection in EEG Signal Using Machine Learning Techniques, Dec. 2017, Australasian College of Physical Scientists and Engineers in Medicine 2017, pp. 1-14.

(Continued)

*Primary Examiner* — Etsub D Berhanu
(74) *Attorney, Agent, or Firm* — Wilson Sonsini Goodrich & Rosati (57) ABSTRACT

The present disclosure provides systems and methods for seizure detection. The method for seizure detection may include receiving a plurality of electroencephalography (EEG) signals over a plurality of channels for a subject, preprocessing the plurality of EEG signals by segmenting the plurality of EEG signals for each channel into a plurality of temporal data segments, extracting a plurality of features from each temporal data segment for each channel, and applying a machine learning algorithm to the plurality of features to perform a seizure binary classification for each temporal data segment for each channel. A control policy may be employed to determine a seizure burden on the aggregated seizure binary classifications. When the seizure burden is equal to or exceeds a threshold, a notification may be generated. The notification may be usable by a healthcare practitioner to assess whether the subject may be at risk of having a seizure.

26 Claims, 6 Drawing Sheets

(56) References Cited

U.S. PATENT DOCUMENTS

| | | | |
|---|---|---|---|
| 2008/0162088 A1* | 7/2008 | DeVaul | A61B 5/0024 |
| | | | 702/190 |
| 2008/0228100 A1* | 9/2008 | Navakatikyan | A61B 5/0476 |
| | | | 600/544 |
| 2009/0062679 A1* | 3/2009 | Tan | A61B 5/04012 |
| | | | 600/544 |
| 2009/0082640 A1* | 3/2009 | Kovach | A61B 5/04001 |
| | | | 600/300 |
| 2010/0049482 A1* | 2/2010 | He | A61B 5/048 |
| | | | 703/2 |
| 2012/0101401 A1 | 4/2012 | Faul et al. | |
| 2013/0053722 A1* | 2/2013 | Carlson | A61B 5/7264 |
| | | | 600/554 |
| 2014/0081347 A1* | 3/2014 | Nelson | A61N 1/36082 |
| | | | 607/45 |
| 2015/0088024 A1 | 3/2015 | Sackellares et al. | |
| 2015/0196246 A1* | 7/2015 | Osorio | A61B 5/4094 |
| | | | 600/301 |
| 2015/0216436 A1* | 8/2015 | Bosl | A61B 5/7264 |
| | | | 600/544 |
| 2016/0000382 A1* | 1/2016 | Jain | A61B 5/4094 |
| | | | 600/545 |
| 2019/0160287 A1 | 5/2019 | Harrer et al. | |

OTHER PUBLICATIONS

Syed Muhammad Usman, et al. Epileptic Seizures Prediction Using Machine Learning Methods, Computational and Mathematical Methods in Medicine, vol. 2017, Article ID 9074759 10 Pages.

Tao Zhang, et al. AR Based Quadratic Feature Extraction in the VMD Domain for the Automated Seizure Detection of EEG Using Random Forest Classifier, Biomedical Signal Processing and Control, Elsevier Ltd. 2016, BSPC-897, 10 Pages.

* cited by examiner

SYSTEMS AND METHODS FOR SEIZURE PREDICTION AND DETECTION

BACKGROUND

Monitoring electroencephalography (EEG) signals is an important task for the early diagnosis in seizures. While analyzing EEG signals plays an important role in monitoring the brain activity of patients, an expert is needed to analyze all EEG recordings to detect seizure activity. This can be tedious and time-consuming, and a timely and accurate diagnosis of seizure activity is essential to initiate therapy and reduce the risk of future seizures and seizure-related complications.

At the moment, machine learning algorithms provide an avenue to classify EEG signals and minimize expert intervention. Though machine learning algorithms require good quality EEG signals to provide effective classification results. Oftentimes, the EEG signals provided to machine learning algorithms need to be optimized to make the machine learning algorithms more effective in predicting seizures.

SUMMARY

There is a need to optimize the quality of EEG signals provided to machine learning algorithms to make them more effective in preventing seizures. To optimize the quality of EEG signals, the EEG signals can be used to build features. Each derived feature can focus on a distinct characteristic of an EEG signal that allows the machine learning algorithm to more easily discern measured EEG signals. Through the combination of using features and then classifying them using machine learning algorithms, allows for a more effective means for predicting seizures. Further, by implementing a control policy and seizure burden calculation after classification, allows for an even greater means of accurately determining seizures by removing false positives or inaccurate readings from the EEG signals provided.

An aspect of the disclosure provides a method for seizure detection. The method may include receiving a plurality of electroencephalography (EEG) signals over a plurality of channels for a subject. The method may further include preprocessing the plurality of EEG signals by segmenting the plurality of EEG signals for each channel into a plurality of temporal data segments. In some cases, the method may extract a plurality of features from each temporal data segment for each channel. In some cases, the method may apply a machine learning algorithm to the plurality of features to perform a seizure binary classification for each temporal data segment for each channel.

In some embodiments, the preprocessing of the plurality of EEG signals may further comprise applying a filter to the plurality of EEG signals over the plurality of channels, prior to the segmentation of the plurality of EEG signals. In some cases, the filter may comprise a bandpass filter configured to filter the plurality of EEG signals between 1 Hz and 35 Hz.

In some embodiments, the seizure binary classification may comprise classifying each temporal data segment for each channel as (1) seizure-positive or (2) seizure-negative. In some cases, each temporal data segment may be associated with a time epoch. In some cases, a cluster of seizure-positive classifications may be indicative of a potential electrographic seizure for the corresponding time epoch. In some cases, the method may further comprise comparing the classifications sequentially across a plurality of time epochs on each channel and discarding a subset of the classifications if the subset comprises fewer than three seizure-positive classifications in a row. In some cases, the method may further comprise classifying a particular time epoch as associated with a potential electrographic seizure, if the temporal data segments for a subset of the plurality of channels are classified as seizure-positive. In some cases, the subset may comprise at least half of the plurality of channels. In some cases, the subset may comprise at least half of the plurality of channels.

In some embodiments, the method may further comprise aggregating the seizure binary classifications for the plurality of temporal data segments for the plurality of channels over a moving time window. In some cases, the moving time window may range from about one minute to ten minutes. In some cases, the moving time window may be about five minutes. In some cases, the plurality of channels may comprise at least three channels. In some cases, the plurality of channels may comprise eight channels. In some embodiments, each temporal data segment may have a duration ranging from about one second to twenty seconds. In some cases, the duration of each temporal data segment may be about ten seconds.

In some embodiments, the plurality of features may comprise time and/or frequency domain features that are intrinsic in the plurality of EEG signals. In some cases, the plurality of features may comprise at least twenty different time and/or frequency features. In some cases, the plurality of features may comprise a plurality of discrete values associated with the time and/or frequency domain features.

In some embodiments, the machine learning algorithm may comprise a random forest, a boosted decision tree, a classification tree, a regression tree, a bagging tree, a neural network, or a rotation forest. In some cases, the machine learning algorithm may be individually applied to the plurality of features extracted for each channel, such that each channel has a separate iteration of the machine learning algorithm.

In some embodiments, the method may further comprise determining a seizure burden for the moving time window based on the aggregated seizure binary classifications. In some cases, the seizure burden may comprise a percentage of the time epochs that are classified as seizure-positive. In some cases, determining the seizure burden may comprise averaging the seizure-positive classifications over the moving time window.

In some embodiments, the method may further comprise generating one or more notifications when the seizure burden is equal to or exceeds one or more thresholds. In some cases, the one or more notifications may be usable by a healthcare practitioner to assess whether the subject is at risk of having a seizure. In some cases, the one or more notifications may be generated in the form of visual, audio, and/or textual alerts. In some cases, a first notification indicative of frequent seizure activity may be generated when the seizure burden is equal to or exceeds a first threshold of 10%. In some cases, a second notification indicative of abundant seizure activity may be generated when the seizure burden is equal to or exceeds a second threshold of 50%. In some cases, a third notification indicative of continuous seizure activity may be generated when the seizure burden is equal to or exceeds a third threshold of 90%.

In another aspect, the present disclosure provides a seizure detection system. The seizure detection system may include a preprocessing module configured to receive a plurality of electroencephalography (EEG) signals over a plurality of channels for a subject. The preprocessing module may also be configured to preprocess the plurality of EEG signals by segmenting the plurality of EEG signals for each channel into a plurality of temporal data segments. The seizure detection system may also include a processing module in communication with the preprocessing module. The processing module may be configured to receive the plurality of temporal data segments corresponding to the plurality of channels. The processing module may be configured to also extract a plurality of features from each temporal data segment for each channel. The processing module may be also configured to apply a machine learning algorithm to the plurality of features to perform a seizure binary classification for each temporal data segment for each channel.

In some embodiments, the seizure detection system may further comprise an output module in communication with the preprocessing module. The output module may be configured to aggregate the seizure binary classifications for the plurality of temporal data segments for the plurality of channels over a moving time window. The output module may be also configured to determine a seizure burden for the moving time window based on the aggregated seizure binary classifications. The output module may be also configured to generate one or more notifications when the seizure burden is equal to or exceeds one or more thresholds.

In another aspect, the present disclosure provides a system comprising one or more computer processors. The system may also comprise memory comprising machine-executable instructions that, upon execution by the one or more computer processors, implements a method for seizure detection. The method may comprise receiving a plurality of electroencephalography (EEG) signals over a plurality of channels for a subject. The method may also comprise preprocessing the plurality of EEG signals by segmenting the plurality of EEG signals for each channel into a plurality of temporal data segments. The method may also further comprise extracting a plurality of features from each temporal data segment for each channel. The method may also further comprise applying a machine learning algorithm to the plurality of features to perform a seizure binary classification for each temporal data segment for each channel.

In another aspect, the present disclosure provides a non-transitory computer readable-medium comprising machine-executable instructions that, upon execution by one or more computer processors, implements a method for seizure detection. The method may comprise receiving a plurality of electroencephalography (EEG) signals over a plurality of channels for a subject. The method may comprise preprocessing the plurality of EEG signals by segmenting the plurality of EEG signals for each channel into a plurality of temporal data segments. The method may include extracting a plurality of features from each temporal data segment for each channel. The method may also include applying a machine learning algorithm to the plurality of features to perform a seizure binary classification for each temporal data segment for each channel.

In another aspect, the present disclosure provides a method for seizure detection. The method may include receiving a plurality of electroencephalography (EEG) signals over a plurality of channels for a subject. The method may also include preprocessing the plurality of EEG signals by segmenting the plurality of EEG signals for each channel into a plurality of temporal data segments. The method may also include extracting a plurality of features from each temporal data segment for each channel. The method may also include applying a machine learning algorithm to the plurality of features to perform a seizure binary classification for each temporal data segment for each channel. The method may also further include determining a seizure burden for the moving time window based on the aggregated seizure binary classifications. The method may also further include presenting the seizure burden to the user.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at most about" or "at least about" precedes the first numerical value in a series of two or more numerical values, the term "at most about" or "at least about" applies to each of the numerical values in that series of numerical values. For example, at most about 3, 2, or 1 is equivalent to at most about 3, at most about 2, or at most about 1.

Overview

Manual inspection of electroencephalography (EEG) brain signals can be a time-consuming and laborious process. Valuable time can be lost manually analyzing such EEG signals when a patient may be experiencing a seizure. Automatic techniques that can analyze EEG signals can help provide a timely and accurate diagnosis of seizure activity to assist clinicians to initiate therapy and reduce the risk of future seizures and seizure-related complications.

Machine learning algorithms provide an avenue to automatically classify EEG signals and minimize expert intervention. Though machine learning algorithms require good quality EEG signals to provide effective classification results. Additionally, the EEG signals provided to the machine learning algorithm may need to be given as features that describe a characteristic of the EEG signal that pertains to seizure activity. Furthermore, post-classification of the features by the machine learning algorithm, a control policy comprising a set of rules along with a seizure burden calculation allows the method and/or system to more accurately depict that the subject is experiencing or potentially experiencing a seizure.

The seizure detection system and methods described herein provide a user with an EEG detection device coupled to a seizure detection module capable of automatic and accurate seizure detection. Additionally, the seizure detection module is capable of notifying the user of an impending/active seizure. The seizure detection module intakes and preprocesses the EEG signals from an EEG device. The EEG signals are then analyzed and valuable EEG features are extracted. The EEG features are classified using a machine learning algorithm module. The classification of the features for a given time epoch are then governed by a control policy to calculate a seizure burden value. If the seizure burden value is equal to or exceeds one or more thresholds, the method and/or system generates one or more notifications that can used by a healthcare practitioner to assess whether the subject may be at risk of having a seizure. Increasing values of seizure burden may be used by a healthcare practitioner as an indication of an increasing severity of seizures. Seizure burden values equal to or exceeding one or more thresholds may be used by a healthcare practitioner as an indication of a medical condition, for example, status epilepticus. The change in seizure burden over time, or the characteristic shape of a seizure burden graph, may be used by a healthcare practitioner to determine the course of treatment for the subject or to evaluate the effectiveness of a course of treatment for the subject.

Seizure Detection Module
I. Signal acquisition and pre-processing
II. Signal analysis
III. Seizure burden calculation and output
IV. Post Seizure Detection
V. Computer systems
I. Signal Acquisition and Pre-Processing
(a) EEG Signals/Acquisition For ease of explanation, the figures and corresponding description below are described below with reference to analysis of signals representing brain activity (e.g., electroencephalography (EEG) signals) and/or heart activity (e.g., electrocardiography (ECG) signals) of a living subject. However, one of skill in the art will recognize that signals representing other bodily functions (e.g., an electromyography (EMG) signal, or an electronystagmography (ENG) signal, a pulse oximetry signal, a capnography signal, and/or a photoplethysmography signal) may be substituted, or used in addition to (e.g., in conjunction with), one or more signals representing brain activity and/or heart activity.

A system for measuring bioelectrical signals may generally comprise one or more electrodes electrically coupled via corresponding conductive wires to a controller and/or output device. In other variations, the electrodes may be coupled to the controller and/or output device wirelessly. The electrodes may be contained within an electrode carrier system that is secured around the head of the patient. The electrode carrier system may be configured as a headband or incorporated into any number of other platforms or positioning mechanisms for maintaining the electrodes against the patient body. Individual electrode assemblies may be spaced apart from one another so that, when the headband is positioned upon the patient's head, the electrode assemblies may be aligned optimally for receiving EEG signals.

The controller and/or output device may generally comprise any number of devices for receiving the electrical signals such as electrophysiological monitoring devices and may also be used in combination with any number of brain imaging devices, e.g., fMRI, PET, NIRS, etc. In one particular variation, the electrode embodiments described herein may be used in combination with devices such as those which are configured to receive electrical signals from the electrodes and process them.

In some embodiments, signals corresponding to brain electrical activity are obtained from a human brain and correspond to electrical signals obtained from a single neuron or from a plurality of neurons. In some embodiments, sensors include one or more sensors affixed (e.g., taped, attached, glued) externally to a human scalp (e.g., extra-cranial sensor). For example, an extra-cranial sensor may include an electrode (e.g., electroencephalography (EEG) electrode) or a plurality of electrodes (e.g., electroencephalography (EEG) electrodes) affixed externally to the scalp (e.g., glued to the skin via conductive gel), or more generally positioned at respective positions external to the scalp Alternatively, dry electrodes can be used in some implementations (e.g., conductive sensors that are mechanically placed against a living subject's body rather than planted within the living subject's body or held in place with a conductive gel). An example of a dry-electrode is a headband with one or more metallic sensors (e.g., electrodes) that is worn by the living subject during use. The signals obtained from an extra-cranial sensor may sometimes be called EEG signals or time-domain EEG signals. In some cases, a sensor may be an accelerometer or an inertial measurement unit (IMU) that may measure the mechanical movement of the subject and/or the device (e.g., produce one or more electrical signals corresponding to mechanical movement of the subject and/or device). The system may be configured to utilize one or more sensors to aid in seizure detection as described elsewhere herein.

Figure 1:
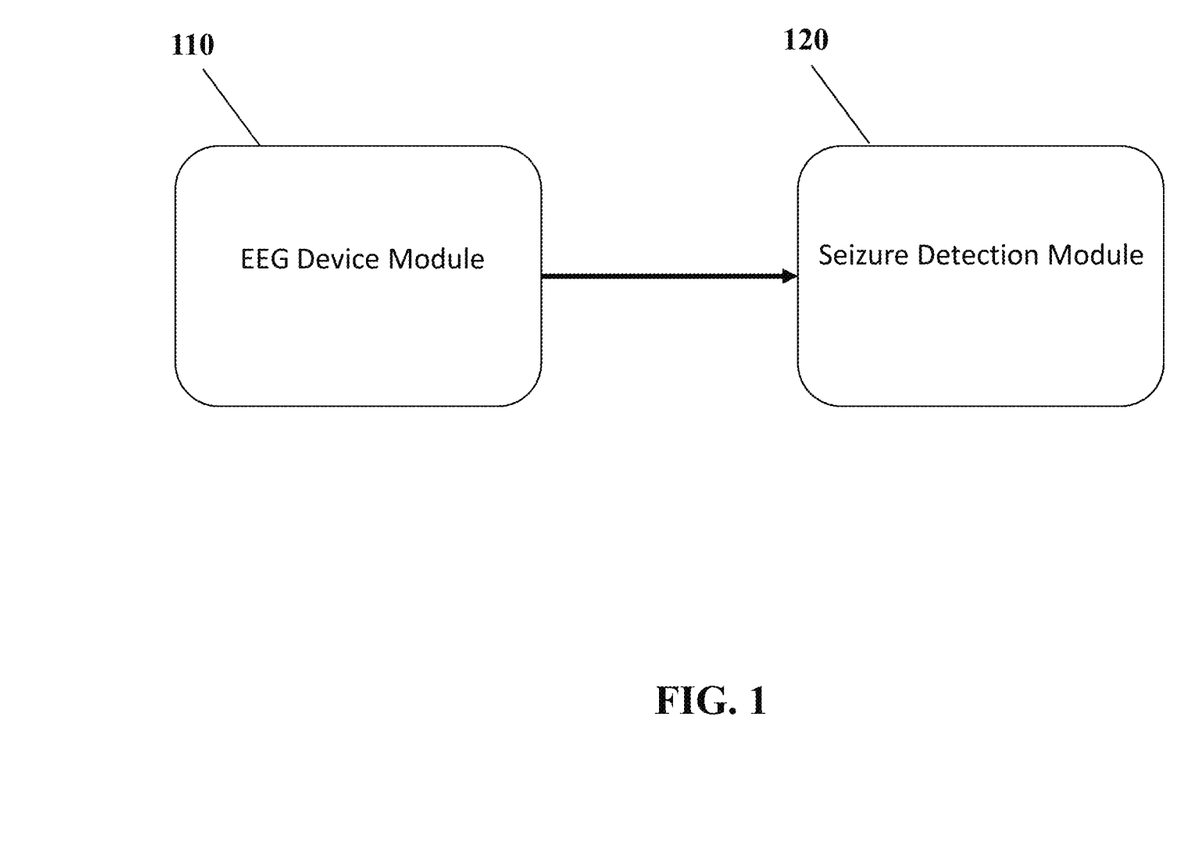
FIG. 1 shows an EEG device configured to provide EEG signals to a seizure detection module, in accordance with embodiments of the present disclosure.
Figure 2:
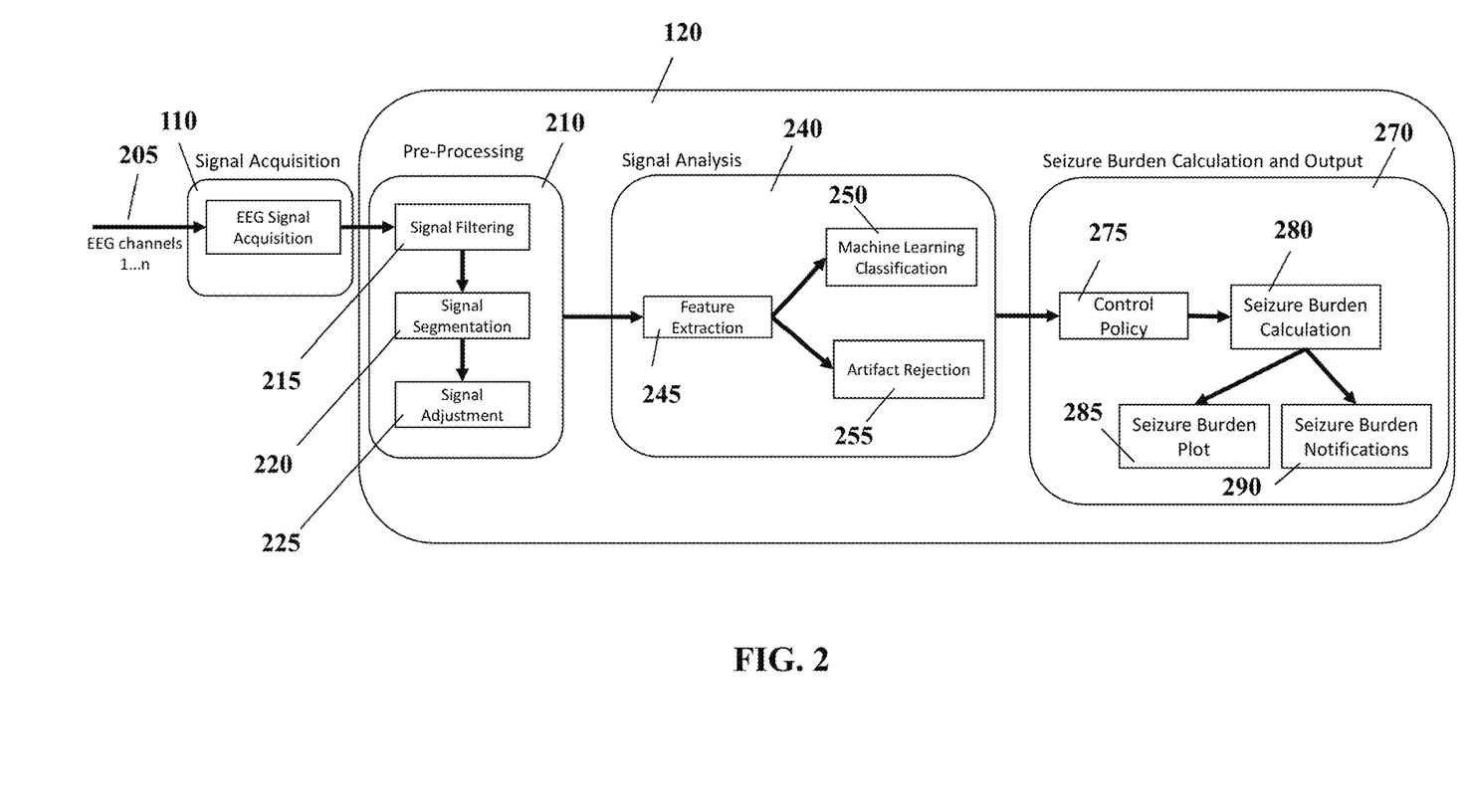
FIG. 2 shows an illustration of the EEG signal work flow for seizure detection, in accordance with embodiments of the present disclosure.

In an aspect, the present disclosure provides a method for seizure detection. In some cases, the method may include receiving a plurality of signals (e.g. EEG signals, EKG signals, EMG signals, etc) over a plurality of channels for a subject. The method may include receiving a plurality of electroencephalography (EEG) signals over a plurality of channels for a subject. The plurality of EEG signals may be provided to a seizure detection module. FIG. 1 shows an illustration of the workflow of EEG signal collection by the EEG device module 110 to the seizure detection module 115. FIG. 2 shows an in-depth illustration of the workflow by the EEG device module and seizure detection module for seizure prediction. As shown in FIG. 2, the seizure detection module can comprise a pre-processing module, signal analysis module, and seizure burden calculation and output module. The EEG device module 110 can have a plurality of channels 205 for EEG signal acquisition from a subject. In some cases, the plurality of channels may have between 1 to 256 channels. In some cases, the plurality of channels may have between 8 to 256 channels. In some cases, the plurality of channels may have more than 256 channels. In some cases, the plurality of channels may have 8, 10, 16, 20, 32, 64, 128, or 256 channels.

(b) Preprocessing of EEG Signals

In some embodiments, the EEG device module may have one or more analog front ends configured to receive sensor EEG signals from sensors. The EEG signals may be preprocessed as described elsewhere herein. In some embodiments, a separate (e.g., independent) analog front end may be provided for interfacing with each of a set of sensors. In some embodiments, one or more analog front ends may be provided for interfacing with a set of EEG sensors.

In some embodiments, the method may include preprocessing the plurality of signals by segmenting the plurality of signals for each channel into a plurality of temporal data segments. In some embodiments, the method may include preprocessing the plurality of EEG signals by segmenting the plurality of EEG signals for each channel into a plurality of temporal data segments. FIG. 2 shows an illustration of the seizure detection module 120. The seizure detection module intakes EEG signals from a plurality of channels from the EEG device module. The seizure detection module may preprocess the EEG signals from a plurality of channels with a preprocessing module 210 configured to preprocess EEG signals. As shown in FIG. 2, the preprocessing module can include a signal filtering module 215, signal segmenting module 220, and signal adjustment module 225.

In some embodiments, the filtering module 215 may be configured to may filter EEG signals from the incoming set of channels from the EEG device module as described elsewhere herein. In some cases, preprocessing may be, for example, segmenting the EEG signals, filtering the EEG signals based on frequency, adjusting the EEG signals, or as described elsewhere herein, etc.

In FIG. 2, the signal segmentation module 220 can be configured to segment EEG signals. In some embodiments, the plurality of EEG signals may be segmented to between 1 to 100000 data segments. In some cases, the number of EEG data segments may depend on the duration of the EEG recordings. In some cases, the number of EEG data segments may be fixed regardless of the duration of the EEG recordings.

In some embodiments, each temporal data segment may have a duration of between about 1 second to 1 hour. In some cases, each temporal data segment may have a duration of between about 1 second to 30 seconds. In some cases, each temporal data segment may have a duration of between about 1 second to 10 seconds. In some cases, the duration of each temporal data segment may be fixed for the entire EEG recording. In some cases, the duration of each temporal data segment may be variable or adaptive during an EEG recording.

In some embodiments, the preprocessing of the plurality of EEG signals may comprise applying one or more filtering steps to the plurality of EEG signals over the plurality of channels. The preprocessing of the plurality of EEG signals may comprise using at least 1 filter, 2 filters, 3 filters, 4 filters, 5 filters, 6 filters, 7 filters, 8 filters, 9 filters, 10 filters, 15 filters or more. The preprocessing of the plurality of EEG signals may comprise using at most about 15 filters, 10 filters, 9 filters, 8 filters, 7 filters, 6 filters, 5 filters, 4 filters, 3 filters, 2 filters or less. The preprocessing of the plurality of EEG signals may comprise using anywhere between 1 to 15 filters, 1 to 10 filters, 1 to 5 filters, or 1 to 3 filters.

In some embodiments, the one or more filtering steps may be applied before, during, and/or after the segmentation of the plurality of EEG signals. One or more of the filtering steps may include, for example, a digital filter, an analogue filter, or a combination thereof. One or more of the filtering steps may include, for example, a bandpass filter, low-pass filter, a high-pass filter, a band-stop filter, an all-pass filter, a Kalman filter, an adaptive filter, or a notch filter, etc. In some cases, the low frequency cutoff of the filters may be between 0.1 Hz and 5 Hz. In some cases, the high frequency cutoff of the filters may be between 5 Hz and 200 Hz. In some cases, the notch filter frequency may match the local power line frequency. In some cases, the notch filter frequency may be 50 Hz or 60 Hz to match the local power line frequency.

In some embodiments, each temporal data segment may be associated with a time epoch. For each corresponding time epoch, a cluster of seizure-positive classifications may be indicative of a potential electrographic seizure. In some cases, a cluster of seizure-positive classifications may comprise of between about 1 to 50 seizure positive classifications. In some cases, a cluster of seizure positive classifications may comprise of between 1 to 10 seizure positive calculations.

In some embodiments, the method may further comprise comparing the classifications sequentially across a plurality of time epochs on each channel. In some cases, before/after/during comparing the classifications sequentially across a plurality of time epochs on each channel, the classifications sequentially across a plurality of time epochs on each channel may be discarded. In some cases, a subset of the classifications may be discarded. In some cases, a subset of fewer than about 1 to 20 classifications may be discarded. In some cases, a subset of fewer than 3 classifications may be discarded.

In some embodiments, the subset of seizure-positive classification may be discarded because, for example, they may be random readings, of low reliability, inaccurate classification, incorrect classification, calibration, system error, disconnected electrodes, artifactual signals, system interference, or other signals, etc.

In some embodiments, the subset of seizure-positive classification may be discarded to, for example, conserve memory space, improve processing speed, reduce energy usage, reduce heat of the system, reduce calculation costs, save processing power, save processing time, increase reliability, or decrease random access memory usage, etc In some embodiments, the greater number of seizure-positive classifications in a row may be indicative of high reliability. The greater the reliability of seizure-positive classifications, the more accurate determination of detecting a seizure in a patient. In some cases, the greater reliability of seizure-positive classifications may be indicative of the machine learning algorithm accuracy, quality of data (EEG signals), or health status of the EEG detecting system, etc. In some embodiments, a particular time epoch may be classified as associated with a potential electrographic seizure if the temporal data segments for a subset of the plurality of channels are classified as seizure-positive. In some cases, the subset may be at least 5%, 10%, 20%, 30%, 40%, 50% or more of the plurality of channels. In some cases, the subset may be at most about 50%, 40%, 30%, 20%, 10%, 5%, or less of the plurality of channels.

(c) EEG Signal Adjustment

FIG. 2 shows a signal adjustment module 225 configured to adjust an EEG signal. In some embodiments, the method may adjust any EEG signal. Adjusting an EEG signal may include, for example, increasing and/or decreasing the amplitude of the EEG signal, adding or decreasing the noise level of the EEG signal, increasing and/or decreasing the time epoch the EEG signal, increasing and/or decreasing the intensity of the EEG signal, increasing and/or decreasing the signal frequency of the EEG signal, increasing and/or decreasing the voltage of the EEG signal, changing the morphology of the EEG signal (e.g. the shape of the EEG signal), increasing and/or decreasing the periodicity of the EEG signal, increasing or decreasing the synchrony of the EEG wave, spectral subtraction, standardizing etc.

In some cases, the EEG signal may be reduced. In some cases, the EEG signal may be down-sampled to a lower sampling frequency. For example, EEG data recorded at a sampling frequency of 500 Hz may be down sampled by a factor of 2 to 250 Hz.

In some cases, the EEG signal may be subjected to bit-width reduction. In some cases, the level of resolution at which the EEG signals are recorded may not be required by the method to achieve accurate seizure detection. In some cases, the bit-width reduction may reduce the EEG signal to a lower number of bits per sample through standard quantization of the EEG signal, for example, from 32 bits per sample to 12 bits per sample. In some cases, bit-width reduction may be advantageous if the method is to be implemented in a portable system, as it may be useful for reducing power consumption due to decreased processing load.

In some cases, spectral subtraction may be used to reduce the amount of additive noise in the EEG signal. In some cases, the noise may be caused by external surroundings. In some cases, the noise may be caused by the measurement equipment. In some cases, the noise may be caused by the user. In some cases, an average frequency spectrum of non-seizure EEG signal may be computed over a period of time to provide a base level estimate of the noise frequency spectrum. In some cases, as the EEG signals are recorded, the EEG signals may be converted to the frequency domain. In some cases, the average noise spectrum may then be subtracted from the EEG frequency spectrum. In some cases, the resulting spectrum and phase information from the original noisy signal may be combined. In some cases, the resulting spectrum may be transformed back into time domain to produce a de-noised signal.

In some embodiments, the EEG signal may be standardized by eliminating the effect of the montage that was used in gathering the EEG signals. In some cases, independent component analysis (ICA) or principal component analysis (PCA) methods may be used to provide the montage elimination. In some cases, the ICA or PCA method may separate the EEG signal into a set of sources independent of the montage used to record them. In some cases, using standardized EEG data may remove errors introduced by the varying practices of clinicians.

In some cases, a non-negative matrix factorisation (NMF) method may be applied to each channel as a form of artifact removal. In some cases, the spectrum of the signal may be decomposed into the extracted bases to obtain weights. In some cases, the spectrum may be reconstructed using the bases of artifacts and the corresponding weights removed from the initial EEG signal.

II. Signal Analysis (a) Feature Extraction

In FIG. 2, the seizure detection module may comprise a signal analysis module. The signal analysis module may comprise a feature extraction module 245 and a machine learning classification module 250. The feature extraction module 245 may be configured to take preprocessed measured data (e.g. EEG signals) from the preprocessing module 210 to build derived values (e.g. features). In some embodiments, feature extraction may start from an initial set of measured data (e.g. EEG signals, EEG signals of a given time epoch, etc) and may build derived values (e.g. features) intended to be informative and non-redundant. In some cases, the feature extraction module may include extracting a plurality of features from each temporal data segment for each channel individually. In some cases, the feature extraction module may include extracting a plurality of features from each temporal data segment for all channels together. In some cases, the feature extraction module may include extracting a plurality of features from each temporal data segment of one or more groupings with each grouping consisting of one or more channels. As shown in FIG. 2, the extracted features can be relayed to a machine learning classification module 250 that may be configured to analyze and classify the extracted features as described elsewhere herein. In some cases, feature extraction may facilitate the subsequent learning and generalization steps of a machine learning algorithm. In some cases, feature extraction may lead to better human interpretations. In some cases, feature extraction may be related to dimensionality reduction.

In some cases, when the input data (e.g. EEG signals) to the machine learning algorithm is too large to be processed and suspected to be redundant (e.g. the same measurement in both Hz and seconds, or the repetitiveness of a characteristic), the data can be transformed into a reduced set of features.

In some cases, determining a subset of the initial features may be called feature selection. In some cases, the selected features may be expected to contain the relevant information from the input data (e.g. EEG signals). In some cases, the selected features may be expected to contain the relevant information from the input data so that the desired task can be performed by using this reduced representation instead of the complete initial data.

In some embodiments, feature extraction may involve reducing the number of resources required to describe a large set of data (e.g. EEG signals). In some cases, analysis with a large number of variables may require a large amount of memory and computation power. In some cases, it may cause a machine learning algorithm to overfit to training samples and generalize poorly to new samples. In some cases, feature extraction may construct combinations of the variables to accurately describe the data with sufficient accuracy. In some cases, feature extraction may construct combinations of the variables to accurately describe the data with sufficient accuracy while preventing overfitting.

In some embodiments, results may be improved using constructed sets of application-dependent features. In some cases, the constructed sets may be built by an expert. In some cases, general dimensionality reduction techniques may be used. In some cases, general dimensionality reduction techniques may be, for example, independent component analysis, isomap, kernel PCA, latent semantic analysis, partial least squares, principal component analysis, multi-factor dimensionality reduction, nonlinear dimensionality reduction, multilinear principal component analysis, multilinear subspace learning, semidefinite embedding, autoencoder, etc.

In some cases, a set of numeric features may be described by a feature vector. In some cases, a feature vector may be an n-dimensional vector of numerical features that represent some object.

In some embodiments, data analysis software packages may provide for feature extraction. In some cases, data analysis software packages may provide for dimension reduction. In some cases, data analysis software packages may include programming environments such as MATLAB, SciLab, NumPy, or the R language, etc. In some cases, a programming language script may be used to extract features from EEG signals. In some cases, the programming language script may be, for example, MATLAB, python, java, javascript, Ruby, C, C++, or Perl, etc.

In some cases, the plurality of features may be intrinsic in the plurality of EEG signals. Intrinsic may be a feature of an EEG signal that may be measured, for example, the amplitude of the EEG signal, the duration of the EEG signal, the variation of the EEG signal, the power of the EEG signal, the local maxima/minima of the EEG signal, the pattern of the EEG signal, the regularity of the EEG signal, the spectral power distribution of the EEG signal, or the frequency of the EEG signal, etc. In some cases, the plurality of features may be a measurement of the power of a signal with a particular frequency. The frequency may be, for example, from about 0 Hz to 100 Hz. In some cases, the power of a signal may be normalized to a total power. In some cases, the power of a signal may be a ratio of power between one or more signals. In some cases, a feature may be a function performed on a signal to obtain a value. For example, a function may measure the root mean square (RMS) of a signal (e.g. EEG signal) to obtain the RMS value of the signal. In some cases, a feature may compare one signal (e.g. EEG signal) to one or more signals. In some cases, a feature may compare one or more signals (e.g. EEG signals) to one or more signals. In some cases, a feature may measure an attribute of a signal (e.g. EEG signal). In some cases, a feature may compare one or more attributes of a signal (e.g. EEG signal) with one or more attributes of a signal. An attribute may be, for example, an intrinsic property of the EEG signal. In some case, the feature of an EEG signal may be continuous and/or discrete in time.

In some cases, the plurality of features may include at least twenty different time and/or frequency features. In some cases, the plurality of features may include at most one thousand time and/or frequency features. In some cases, the plurality of features may include between about 10 features to 200 features. In some cases, the plurality of features may include between about 10 features to 100 features. In some cases, the plurality of features may include between about 10 features to 50 features.

In some cases, the plurality of features may include a plurality of discrete values associated with the time domain, frequency domain, time-frequency domain, information theory, and nonlinear-dynamics system theory features. In some cases, the plurality of features may include a plurality of discrete values associated with the time and/or frequency domain features. The plurality of features may include a plurality of continuous values associated with the time and/or frequency domain features.

In some cases, the plurality of signals may be converted into a digital signal. In some cases, the plurality of signal may be converted into a digital signal and then an analog signal.

In some cases, the features may be sampled from a portion of the EEG signal. Features may be sampled from a portion of the EEG signal to reduce processing time and power required.

In some embodiments, a feature may be pertaining to a certain weight value. The weight value may give one feature a higher score for detecting a seizure. The higher score may indicate that the feature may be more relevant in predicting seizure activity. The method may adjust the weight value of any feature at any given time. The method may adjust by increasing and/or decreasing the weight value of any feature at any given time.

(b) Classification Using Machine Learning

In some embodiments, the method may include applying a machine learning algorithm to the plurality of features to perform a seizure classification for each temporal data segment for each channel individually. In some cases, the machine learning classification module may include performing seizure classification for each temporal data segment for all channels together. In some cases, the machine learning classification module may include performing seizure classification for each temporal data segment of one or more groupings with each grouping consisting of one or more channels. FIG. 2 shows the machine learning classification module 250 that may take the features collected/extracted from the preprocessing step and classify the features. In some cases, the features may be extracted without a preprocessing step.

In some cases, machine learning algorithms may need to extract and draw relationships between features as conventional statistical techniques may not be sufficient. In some cases, machine learning algorithms may be used in conjunction with conventional statistical techniques. In some cases, conventional statistical techniques may provide the machine learning algorithm with preprocessed features.

In some embodiments, the plurality of features may be classified into any number of categories. A temporal segment may be classified as, for example, seizure-positive, seizure-negative, seizure-like, uncertain seizure activity, etc. In some cases, the plurality of features may be classified into between 1 to 20 categories. Individual categories may also be divided into sub-categories. For example, a temporal segment classified as seizure-positive may be further subdivided into focal versus generalized seizure events.

In some embodiments, the method may include applying a machine learning algorithm to the plurality of features to perform a seizure binary classification for each temporal data segment for each channel.

In some embodiments, the one or more features collected may be discarded prior to or during machine learning classification.

In some embodiments, a human may select, and discard features prior/during machine learning classification. In some cases, a computer may select and discard features. In some cases, the features may be discarded based on a threshold value.

In some embodiments, any number of features may be classified by the machine learning algorithm. The machine learning algorithm may classify at least 10 features. In some cases, the plurality of features may include between about 10 features to 200 features. In some cases, the plurality of features may include between about 10 features to 100 features. In some cases, the plurality of features may include between about 10 features to 50 features In some embodiments, the machine learning algorithm may be, for example, an unsupervised learning algorithm, supervised learning algorithm, or a combination thereof. The unsupervised learning algorithm may be, for example, clustering, hierarchical clustering, k-means, mixture models, DBSCAN, OPTICS algorithm, anomaly detection, local outlier factor, neural networks, autoencoders, deep belief nets, hebbian learning, generative adversarial networks, self-organizing map, expectation-maximization algorithm (EM), method of moments, blind signal separation techniques, principal component analysis, independent component analysis, non-negative matrix factorization, singular value decomposition, or a combination thereof. The supervised learning algorithm may be, for example, support vector machines, linear regression, logistic regression, linear discriminant analysis, decision trees, k-nearest neighbor algorithm, neural networks, similarity learning, or a combination thereof. In some embodiments, the machine learning algorithm may comprise a deep neural network (DNN). The deep neural network may comprise a convolutional neural network (CNN). The CNN may be, for example, U-Net, ImageNet, LeNet-5, AlexNet, ZFNet, GoogleNet, VGGNet, ResNet18 or ResNet, etc. Other neural networks may be, for example, deep feed forward neural network, recurrent neural network, LSTM (Long Short Term Memory), GRU (Gated Recurrent Unit), Auto Encoder, variational autoencoder, adversarial autoencoder, denoising auto encoder, sparse auto encoder, boltzmann machine, RBM (Restricted BM), deep belief network, generative adversarial network (GAN), deep residual network, capsule network, or attention/transformer networks, etc.

In some embodiments, the machine learning algorithm may be, for example, a random forest, a boosted decision tree, a classification tree, a regression tree, a bagging tree, a neural network, or a rotation forest. The machine learning algorithm may be individually applied to the plurality of features extracted for each channel, such that each channel may have a separate iteration of the machine learning algorithm.

In some embodiments, the method may apply one or more machine learning algorithms. In some embodiments, the method may apply one or more one machine learning algorithms per channel.

In FIG. 2, the machine learning classification module 250 may comprise any number of machine learning algorithms. In some embodiments, the random forest machine learning algorithm may be an ensemble of bagged decision trees. In some cases, the ensemble of bagged decision trees may classify each temporal data segment for each channel as (1) seizure-positive or (2) seizure-negative. The ensemble may be at least about 1, 2, 3, 4, 5, 10, 20, 30, 40, 50, 60, 70, 80, 90, 100, 120, 140, 160, 180, 200, 250, 500, 1000 or more bagged decision trees. The ensemble may be at most about 1000, 500, 250, 200, 180, 160, 140, 120, 100, 90, 80, 70, 60, 50, 40, 30, 20, 10, 5, 4, 3, 2 or less bagged decision trees. The ensemble may be from about 1 to 1000, 1 to 500, 1 to 200, 1 to 100, or 1 to 10 bagged decision trees.

In some embodiments, the method may include applying a machine learning classifier to any number of channels. The method may include applying a machine learning classifier to at least about 1, 2, 3, 4, 5, 6, 7, 8, 9, 10, 15, 20, 25, 50, 100, 500, 1000 or more channels. The method may include applying a machine learning classifier to at most about 1000, 500, 100, 50, 25, 20, 15, 10, 9, 8, 7, 6, 5, 4, 3, 2 or less channels. The method may include applying a machine learning classifier from about 1 to 1000, 1 to 100, 1 to 25, or 1 to 5 channels.

In some embodiments, the method may include applying a machine learning classifier to a subset of channels. The subset of channels may be at least about 1%, 5%, 10%, 20%, 30%, 40%, 50% or more of the total set of channels. The subset of channels may be at most about 50%, 40%, 30%, 20%, 10%, 5%, 1% or less of the total set of channels. The subset of channels may be from about 1% to 50%, 1% to 40%, 1% to 30%, 1% to 20%, 1% to 10%, or 1% to 5% of the total set of channels.

In some embodiments, the machine learning algorithm may have a variety of parameters. The variety of parameters may be, for example, learning rate, minibatch size, number of epochs to train for, momentum, learning weight decay, or neural network layers etc.

In some embodiments, the learning rate may be between about 0.00001 to 0.1.

In some embodiments, the minibatch size may be at between about 16 to 128.

In some embodiments, the neural network may comprise neural network layers. The neural network may have at least about 2 to 1000 or more neural network layers.

In some embodiments, the number of epochs to train for may be at least about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 500, 1000, 10000, or more.

In some embodiments, the momentum may be at least about 0.1, 0.2, 0.3, 0.4, 0.5, 0.6, 0.7, 0.8, 0.9 or more. In some embodiments, the momentum may be at most about 0.9, 0.8, 0.7, 0.6, 0.5, 0.4, 0.3, 0.2, 0.1, or less.

In some embodiments, learning weight decay may be at least about 0.00001, 0.0001, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, or more. In some embodiments, the learning weight decay may be at most about 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, 0.001, 0.0001, 0.00001, or less.

In some embodiments, the machine learning algorithm may use a loss function. The loss function may be, for example, regression losses, mean absolute error, mean bias error, hinge loss, Adam optimizer and/or cross entropy.

In some embodiments, the parameters of the machine learning algorithm may be adjusted with the aid of a human and/or computer system.

In some embodiments, the machine learning algorithm may prioritize certain features. The machine learning algorithm may prioritize features that may be more relevant for detecting seizures. The feature may be more relevant for detecting seizures if the feature is classified more often than another feature. In some cases, the features may be prioritized using a weighting system. In some cases, the features may be prioritized on probability statistics based on the frequency and/or quantity of occurrence of the feature. The machine learning algorithm may prioritize features with the aid of a human and/or computer system.

In some embodiments, one or more of the features may be used with machine learning or conventional statistical techniques to determine if a segment is likely to contain artifacts. FIG. 2 shows the artifact rejection module 255 which identifies segments containing artifacts. The identified artifacts may be a result of electrical interference, electrode instability or movement, subject movement, subject eye movement or blinking, subject chewing, subject muscle tensing, subject electrocardiographic artifact, etc. In some cases, movement sensors or other sensors may be used as an additional input to the artifact rejection module. In some cases, the identified artifacts can be rejected from being used in seizure classification. In some cases, the identified artifacts can be reduced, cancelled, or eliminated and the remaining signal may still be processed for seizure classification.

In some cases, the machine learning algorithm may prioritize certain features to reduce calculation costs, save processing power, save processing time, increase reliability, or decrease random access memory usage, etc.

III. Seizure Burden Calculation and Output (a) Control Policy and Seizure Burden In some embodiments, the seizure binary classification may include classifying each temporal data segment for each channel as (1) seizure-positive or (2) seizure-negative. The seizure binary classification may use machine learning algorithms as described elsewhere herein. The method may include aggregating the seizure binary classifications for the plurality of temporal data segments for the plurality of channels over a moving time window. The aggregated seizure classifications may be subjected to a control policy module 275 of the seizure burden calculation and output module 270, as shown in FIG. 2. FIG. 2 shows the seizure burden calculation and output module 270. As shown in FIG. 2, the seizure burden calculation and output module 270 may comprise a control policy module 275, a seizure burden calculation module 280, a seizure burden plot module 285, and a seizure burden notification module 290. The control policy module 275 may be configured to implement a control policy, the seizure burden calculation module 280 may be configured to calculate a seizure burden value, the seizure burden plot module 285 may be configured to plot seizure burden values, and the seizure burden notification module 290 may be configured to provide notifications as described elsewhere herein, respectively.

In some cases, the moving window may have a period of time between 1 minute and 1 hour. In some cases, the period of time of the moving window may be dynamic or adjustable instead of fixed. In some cases, the period of time of the moving window may be dependent on the subject.

In some embodiments, a cluster of seizure-positive classifications on one or more channels may be subjected to a control policy module 275 to result in an overall determination of a seizure for the patient for a corresponding time epoch.

The control policy may be a set of rules that result in an overall determination of seizure for the patient for a corresponding time epoch. The control policy may take a set of parameters as input and act on the set of parameters according to the set of rules to result in an overall determination of a seizure for the patient for a corresponding time epoch. The set of rules may be as described elsewhere herein. The set of rules may be adjusted at any point of time to act on more parameters or to act on less parameters. The set of rules may be adjusted at any point of time to include more rules or to remove rules. The set of rules may be at least about 1, 2, 3, 4, 5, 6 7, 8, 9, 10, 15, 20, 25, 50, 100, 500, 1000, or more rules. The set of rules may be at most about 1000, 500, 100, 50, 25, 20, 15, 10, 9, 8, 7, 6, 5, 4, 3, 2 or less rules. The set of rules may be from about 1 to 1000, 1 to 500, 1 to 100, 1 to 25, 1 to 10, 1 to 5, or 1 to 3 rules.

In some embodiments, the input of parameters for the control policy may include, the quantity of classification of channels as seizure-positive, the quantity of classification of channels as seizure-negative, the classification of channels as seizure-positive, the classification of channels as seizure-negative, the corresponding time epoch, the quantity of channels, the machine learning algorithm used for classification, a moving window time length, the quality of the connection of each channel, information derived from EKG signals, information derived from EMG signals, information regarding the patient's demographics, information regarding the patient's current or previous condition, information regarding treatments or medications applied to the patient, information derived from movement sensors (e.g. an accelerometer or inertial measurement unit), etc.

In some embodiments, the control policy may have any number input of parameters. The control policy may have an input of at least about 1, 2, 3, 4, 5, 6, 7, 8, 9, 10, 11, 12, 13, 14, 15, 20, 25, 50, 100, 500 1000 or more parameters. The control policy may have an input of at most about 1000, 500, 100, 50, 25, 20, 15, 14, 13, 12, 11, 10, 9, 8, 7, 6, 5, 4, 3, 2 or less parameters. The control policy may have an input from about 1 to 1000, 1 to 500, 1 to 100, 1 to 50, 1 to 25, 1 to 15, 1 to 10, or 1 to 5 parameters.

In some embodiments, the set of rules may dictate that the control policy discards the classification of a channel. For example, if the control policy receives an input of a single a seizure-positive classification for a corresponding time epoch, the set of rules may discard the seizure-positive classification for the corresponding time epoch. In some cases, the control policy may receive at least about 1, 2, 3, 4, 5, 6, 7, 8, 9, 10, 50, 100, 500, or more seizure-positive classifications and the set of rules may discard each seizure-positive classification for the corresponding time epoch. In some cases, the control policy may receive at most about 500, 100, 50, 10, 9, 8, 7, 6, 5, 4, 3, 2 or less seizure-positive classifications and the set of rules may discard each seizure-positive classification for the corresponding time epoch. In some cases, the control policy may receive from about 1 to 500, 1 to 100, 1 to 50, 1 to 10, or 1 to 5 seizure-positive classifications and the set of rules may discard each seizure-positive classification for the corresponding time epoch.

In some embodiments, the set of rules may dictate that the control policy output a seizure-positive classification for a set of channels corresponding to a time epoch. For example, if the control policy receives a set of four or more channels that each register a seizure-positive classification for the corresponding time epoch, the set of rules may output a seizure-positive classification for the corresponding time epoch. In some cases, the control policy may receive a set of seizure-positive classifications of at least about 1, 2, 3, 4, 5, 6, 7, 8, 9, 10, 15, 20, 25, 50, 100, 1000 or more channels, the set of rules may output a seizure-positive classification for the set of seizure-positive classifications for the corresponding time epoch. In some cases, the control policy may receive a set of seizure-positive classifications of at most about 1000, 100, 50, 25, 20, 15, 10, 9, 8, 7, 6, 5, 4, 3, 2, or less channels, the set of rules may output a seizure-positive classification for the set of seizure-positive classifications for the corresponding time epoch. In some cases, the control policy may receive a set of seizure-positive classifications from about 1 to 1000, 1 to 500, 1 to 100, 1 to 50, 1 to 25, 1 to 10, or 1 to 5, the set of rules may output a seizure-positive classification for the set of seizure-positive classifications for the corresponding time epoch.

In some embodiments, the method may include calculating the seizure burden of the patient as the percentage of seizure-positive classifications within a specified period of time. As shown in FIG. 2, the seizure burden calculation module 280 may be configured to calculate the seizure burden of the patient. In some cases, the period of time used for seizure burden calculation may be between 1 minute and 1 hour. In some cases, the period of time used for seizure burden calculation may be the entirety of the recording session. In some cases, the period of time used for seizure burden calculation may be dynamic or adjustable instead of fixed.

In some embodiments, the seizure burden may form a continuous output measure by calculating seizure burden for a moving window of time to result in a seizure burden value for individual sequential periods of time. In some cases, the period of time of the moving window may be between 1 minute and 1 hour. In some cases, the period of time of the moving window may be dynamic or adjustable instead of fixed. In some cases, the sequential periods of time formed by the moving window may be overlapping. In some cases, sequential periods of time formed by the moving window may be non-overlapping. In some cases, the moving window may move in time increments between 1 second and 1 hour. In some cases, the moving window may pause or skip periods of time such that the resulting seizure burden values are not continuous or not sequential in time.

Figure 3:
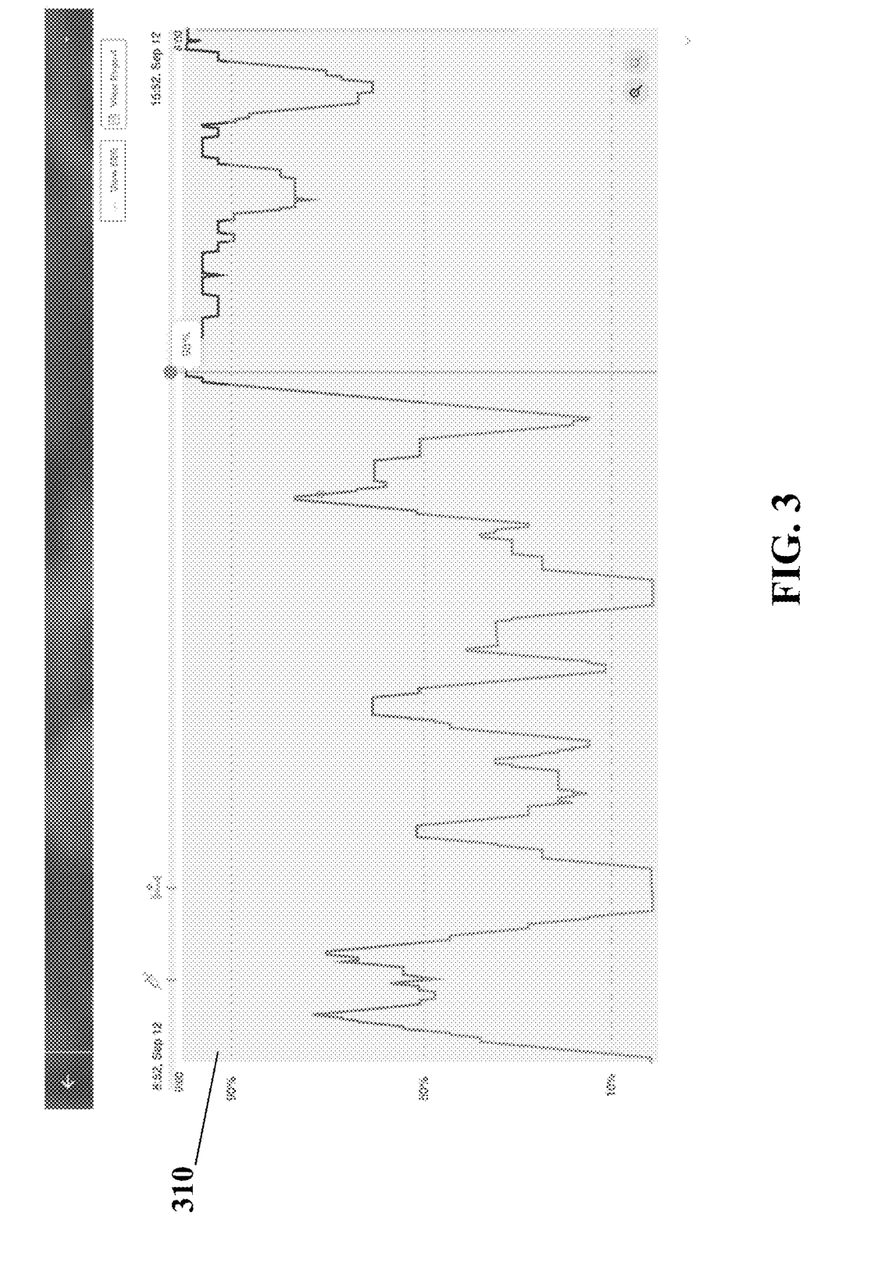
FIG. 3 shows a seizure burden graph, in accordance with embodiments of the present disclosure.

FIG. 2 shows a seizure burden plot module 285 configured to plot the seizure burden of a subject. As shown in FIG. 3, the seizure burden output may be displayed to the user as a time-series plot 310 where each point represents the seizure burden for a period of time. In some embodiments, the seizure burden output may display the one or more thresholds (e.g. 10%, 50%, 90%, etc) to the user on the time-series plot. In some embodiments, the seizure burden output may be displayed to the user as a time-series plot, bar graph, or chart etc. In some embodiments, the time-series plot may be depicted in a certain color to note the threshold that has been passed. As shown in FIG. 3, when the time-series plot of the seizure burden passes the 50% threshold for a period of time, the time-series plot may change from gray to orange. In some cases, when the time-series plot passes 90%, the time-series plot may change from orange to red. The time-series plot may be of any color and the passing of a threshold may be illustrated in any color. In some cases, the seizure burden plot module may display a wide variety of information, for example, the time period measured, the date, or the initial time acquisition, etc. In some cases, the seizure burden plot may be usable by a healthcare practitioner to assess the condition of the subject and determine a course of treatment. The seizure burden plot may also be usable by a healthcare practitioner to monitor the progression of the subject's condition over time or to monitor the effectiveness of courses of treatment.

Figure 4:
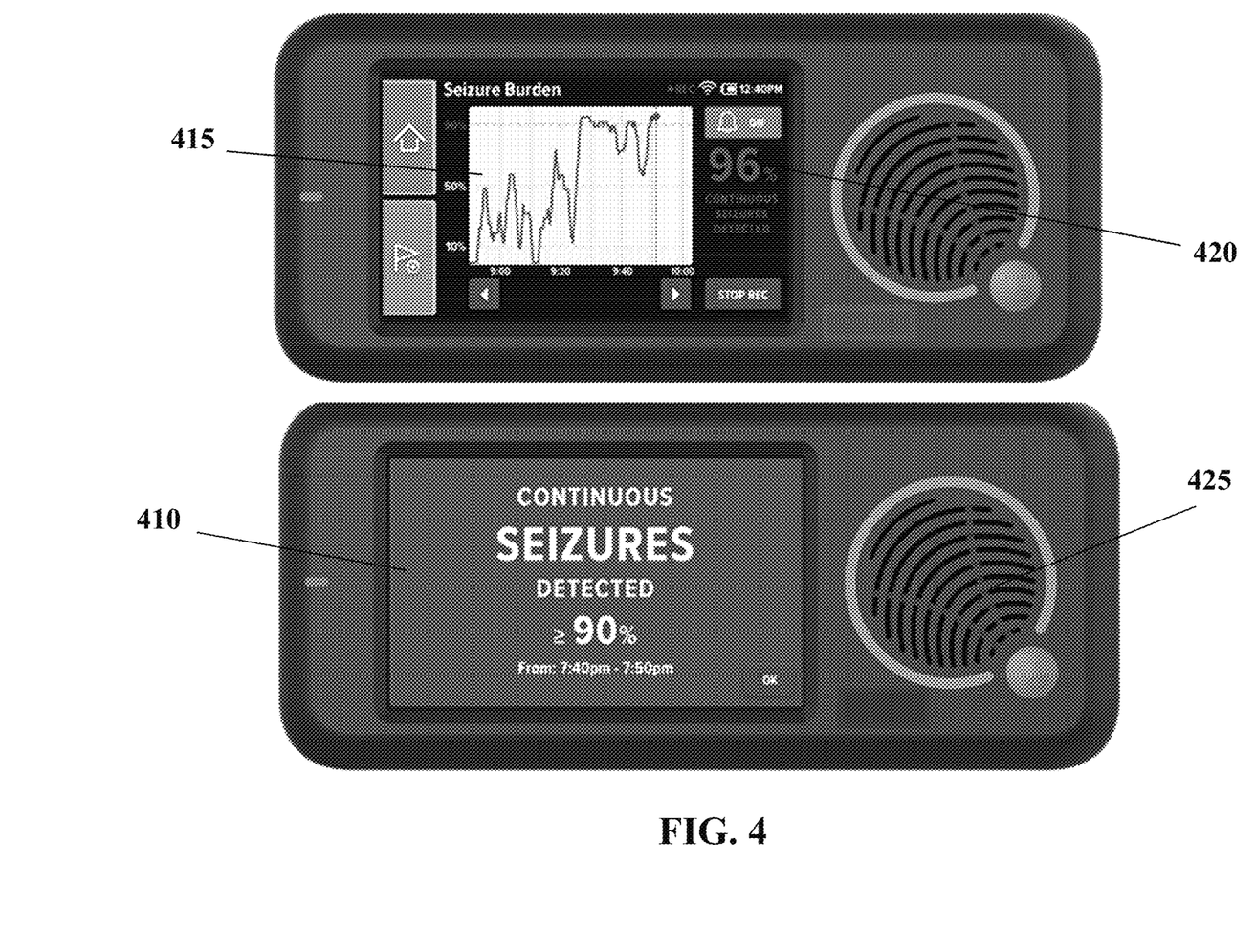
FIG. 4 shows an illustration of the EEG device with a display visualization of the seizure detection output, in accordance with embodiments of the present disclosure.

FIG. 2 shows a seizure burden notifications module 290 configured to generate notifications. In some embodiments, the method may include generating one or more notifications when seizure-positive classifications have been made or when the seizure burden value is equal to or exceeds one or more thresholds. As shown in FIG. 4, when the seizure burden value is equal to or exceeds a threshold (e.g. the 90% threshold), the system may display to a subject (e.g. patient) or user (e.g. healthcare practitioner, doctor, nurse, etc) a notification 410 that the system has detected continuous seizure activity. The notification may also include any color. For example, the background of the screen displaying the notification may be red. The text of the notification may be any color, for example, white. The color of the background of the screen may correlate with the value of the seizure burden calculation. For example, if the seizure burden is equal to or above a certain threshold, the selected color for the background of the screen may indicate that the seizure burden is equal to or above a threshold. The color of the text of the notification may correlate with the value of the seizure burden calculation. For example, if the seizure burden is equal to or above a certain threshold, the selected color for the text of the notification may indicate that the seizure burden is equal to or above a threshold.

The system may also display a wide variety of information to the subject or user in addition to the notification of detected continuous seizure activity. The system may display the seizure burden plot 415, the percentage of seizure burden calculated 420, the time period for which the continuous seizure activity was detected (e.g. 7:40 pm to 7:50 pm), etc. The one or more notifications may be usable by a healthcare practitioner to assess the condition of the subject and determine a course of treatment. In some cases, one or more notifications may be generated when the seizure burden value is equal to or exceeds one or more thresholds as described elsewhere herein. In some cases, the one or more notifications may be generated in the form of visual, audio, and/or textual alerts. The device may include speakers 425 to provide audio notifications. In some cases, the one or more notifications may be delivered via networked communication technology such as the internet, telephone, facsimile, pager, short message service, etc. In some cases, the form, content, or delivery mechanism of the one or more notifications generated may depend on the seizure burden value. In some cases, the user may be able to select the form, content, or delivery mechanism of the one or more notifications generated.

Figure 5:
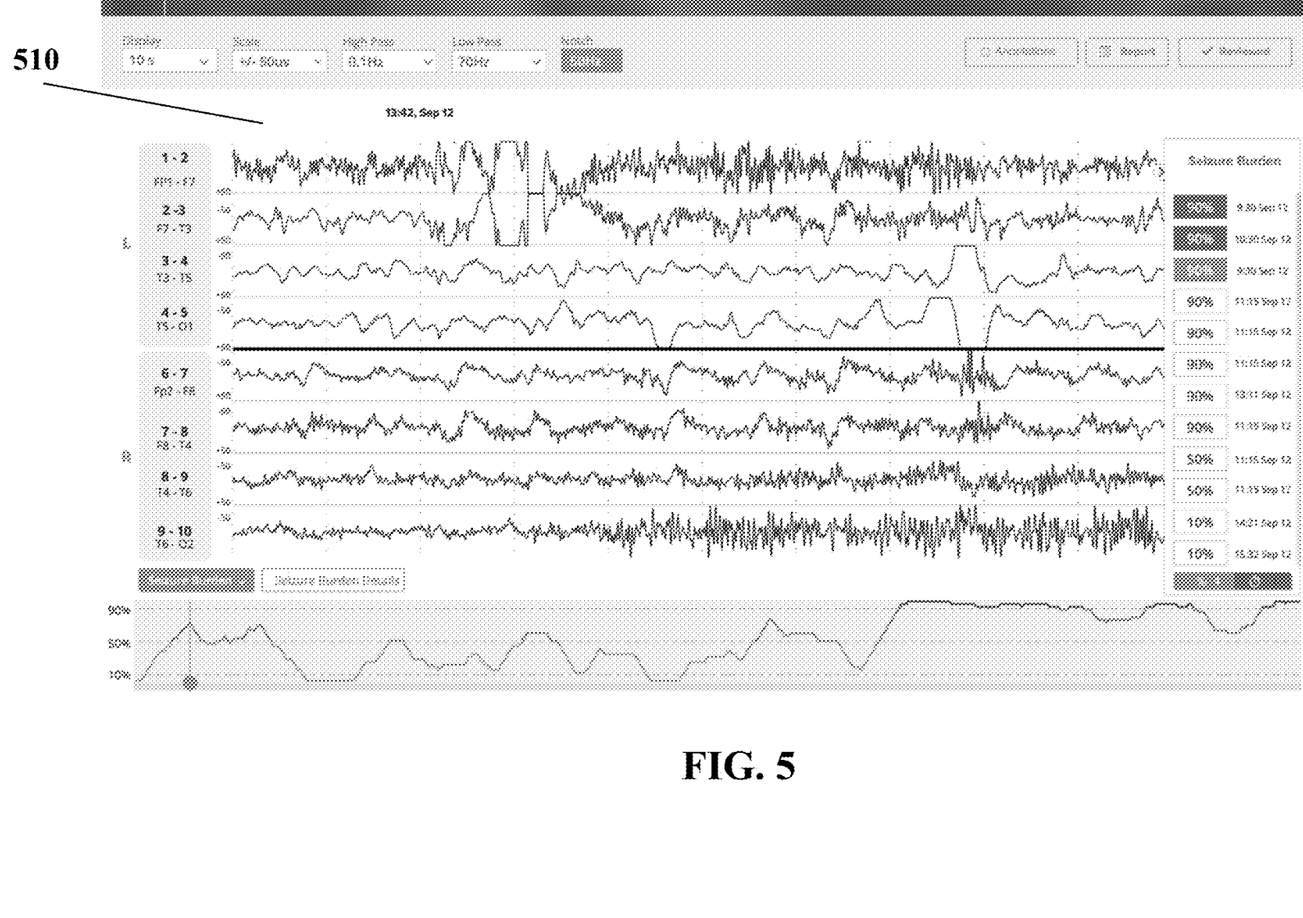
FIG. 5 shows an illustration of the EEG device software with the a display visualization of the seizure detection output, in accordance with embodiments of the present disclosure.

FIG. 5 shows an illustration showing seizure detection output 510 provided by the methods and systems described herein. The interface may provide indication of the EEG signal activity for the plurality of channels from the EEG device module 110. FIG. 5 shows examples of parameters that a user may adjust, for example, the time display, the scale, the high pass frequency, the low pass frequency, or the notch value, etc. The interface may also provide a seizure burden plot as described elsewhere herein. The interface may also provide seizure burden results over different time periods. The interface may also depict the seizure determination for each time segment. The interface may also provide a mechanism for the user to accept or reject the algorithm derived seizure determination or seizure burden calculation. The interface may also provide a mechanism for the user to input their own determination of seizure containing segments or seizure burden. In some cases, the seizure burden may be adjusted as a result of user entered information regarding seizure episodes or seizure burden. The displayed seizure burden and seizure burden notifications may be based solely on algorithm derived seizure determination, solely on user entered seizure determination, or on a combination of algorithm and user seizure determination.

In some embodiments, the seizure burden calculation module may calculate a seizure burden value. The seizure burden notification module may output a notification if the seizure burden value crosses a threshold value. For example, if the seizure burden value crosses a threshold of 10%, a notification may be generated. In another example, if the seizure burden value crosses a threshold of 50%, a notification may be generated. In another example, if the seizure burden value crosses a threshold of 90%, a notification may be generated. In some cases, a first notification indicative of frequent seizure activity may be generated when the seizure burden is equal to or exceeds a first threshold of 10%. In some cases, a second notification indicative of abundant seizure activity may be generated when the seizure burden is equal to or exceeds a second threshold of 50%. In some cases, a third notification indicative of continuous seizure activity may be generated when the seizure burden is equal to or exceeds a third threshold of 90%. In some cases, notifications may be generated to a specific person that the method is programmed to notify.

In some embodiments, the threshold for notification may be of any percentage. The threshold for notification may be at least about 1%, 5%, 10%, 15%, 20%, 25%, 30%, 35%, 40%, 45%, 50%, 55%, 60%, 65%, 70%, 80%, 90%, 95%, 99% or more. The threshold for notification may be at most about 99%, 95%, 90%, 85%, 80%, 75%, 70%, 65%, 60%, 55%, 50%, 45%, 40%, 35%, 30%, 25%, 20%, 15%, 10%, 5%, 1% or less. The threshold for notification may be from about 0% to 100%, 1% to 99%, 5% to 95%, 10% to 90%, 20% to 80%, 30% to 70%, or 40% to 60%. The threshold for notification may also be user adjustable.

In some embodiments, the seizure burden notification module may have any number of thresholds. The seizure burden notification module may have at least about 1, 2, 3, 4, 5, 6, 7, 8, 9, 10, 15, 20, 25, 50, 100, 500, 1000, 5000 or more thresholds. The seizure burden notification module may have at most about 5000, 1000, 500, 100, 50, 25, 20, 15, 10, 9, 8, 7, 6, 5, 4, 3, 2 or less. The seizure burden notification module may have from about 1 to 5000, 1 to 1000, 1 to 500, 1 to 100, 1 to 50, 1 to 25, 1 to 10, or 1 to 5 thresholds. The quantity of thresholds may be increased or decreased at any point in time.

In some embodiments, the seizure burden notification module may provide any number of notifications. The seizure burden notification module may provide at least about 1, 2, 3, 4, 5, 6, 7, 8, 9, 10, 15, 20, 25, 30, 35, 40, 50, 100, 500, 1000 or more notifications. The seizure burden notification module may provide at most about 1000, 500, 100, 50, 40, 35, 30, 25, 20, 15, 10, 9, 8, 7, 6, 5, 4, 3, 2 or less notifications. The seizure burden notification module may provide from about 1 to 1000, 1 to 500, 1 to 100, 1 to 50, 1 to 25, 1 to 10, or 1 to 5 notifications.

In some embodiments, the seizure burden calculation and output module may criteria in addition to the seizure burden threshold to output a notification. In some cases, the duration of time that seizure burden is over a threshold may be used to determine if a notification is output. In some cases, amount of time since the previous crossing of a seizure burden threshold may be used to determine if a notification is output. In some cases, dynamic criteria may be applied with a combination of time based, seizure burden based, and other policies to determine if a notification is output.

In some embodiments, the system may be coupled with other systems. In some cases, the systems may be eye trackers, movement sensors (e.g. an accelerometer or an inertial measurement unit), electromyography (EMG), electrocardiogram (ECG or EKG), etc.

IV. Post Seizure Detection

In some embodiments, the method may include generating one or more notifications as described elsewhere herein.

In some embodiments, the method may provide a user a response to minimize or prevent the detected seizure. The method may provide a response to minimize or reduce the risk of the onset of a seizure. In some cases, a therapeutic may be delivered to the subject to prevent and/or mitigate the predicted seizure. In some cases, a neuromodulation signal pattern may be applied to the subject to prevent and/or mitigate the predicted seizure. In some cases, the method may adjust the neuromodulation or quantity of therapeutic delivered to the subject.

V. Computer Systems

The present disclosure provides computer systems that are programmed to implement methods of the disclosure, including the control of the seizure detection system, control hardware components, receive and process data, interface with a user, etc. A seizure detection system and its various components may include computer hardware (and associated firmware) that may be electrically connected to a computer control system. A control unit may include such a computer system.

Figure 6:
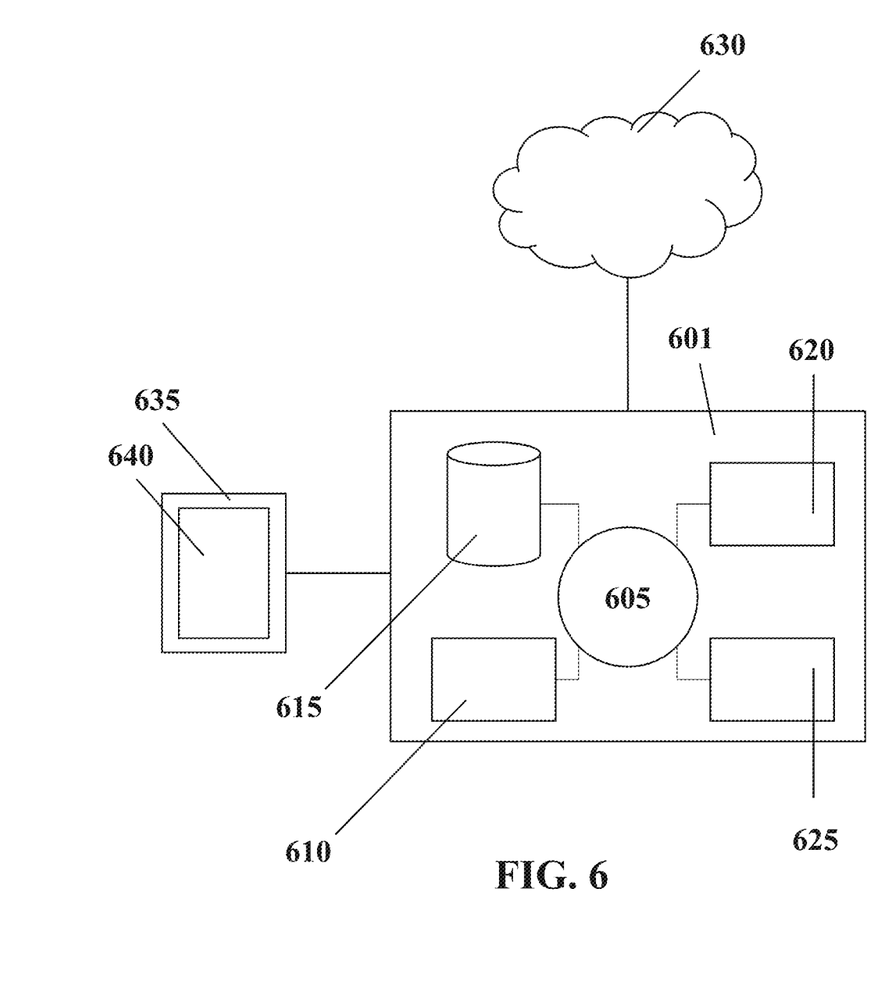
FIG. 6 shows a computer system that is programmed or otherwise configured to implement methods provided herein, in accordance with embodiments of the present disclosure.

FIG. 6 shows a computer system 601 that is programmed or otherwise configured to operate and/or control the EEG device module and the seizure detection module. The computer system 601 can regulate various aspects of the seizure detection system of the present disclosure, such as, for example, processing EEG signals, segmenting EEG signals, extracting features, processing features with machine learning algorithms, implementing the control policy and seizure burden, calculating the seizure burden value, plotting the seizure burden, providing notifications, etc. The computer system 601 can be an electronic device of a user or a computer system that is remotely located with respect to the electronic device. The electronic device can be a mobile electronic device.

The computer system 601 includes a central processing unit (CPU, also "processor" and "computer processor" herein) 605, which can be a single core or multi core processor, or a plurality of processors for parallel processing. The computer system 601 also includes memory or memory location 610 (e.g., random-access memory, read-only memory, flash memory), electronic storage unit 615 (e.g., hard disk), communication interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 can be a data storage unit (or data repository) for storing data. The computer system 601 can be operatively coupled to a computer network ("network") 630 with the aid of the communication interface 620. The network 630 can be the Internet, an internet and/or extranet, or an intranet and/or extranet that is in communication with the Internet. The network 630 in some cases is a telecommunication and/or data network. The network 630 can include one or more computer servers, which can enable distributed computing, such as cloud computing. The network 630, in some cases with the aid of the computer system 601, can implement a peer-to-peer network, which may enable devices coupled to the computer system 601 to behave as a client or a server.

The CPU 605 can execute a sequence of machine-readable instructions, which can be embodied in a program or software. The instructions may be stored in a memory location, such as the memory 610. The instructions can be directed to the CPU 605, which can subsequently program or otherwise configure the CPU 605 to implement methods of the present disclosure. Examples of operations performed by the CPU 605 can include fetch, decode, execute, and writeback.

The CPU 605 can be part of a circuit, such as an integrated circuit. One or more other components of the system 601 can be included in the circuit. In some cases, the circuit is an application specific integrated circuit (ASIC).

The storage unit 615 can store files, such as drivers, libraries and saved programs. The storage unit 615 can store user data, e.g., user preferences and user programs. The computer system 601 in some cases can include one or more additional data storage units that are external to the computer system 601, such as located on a remote server that is in communication with the computer system 601 through an intranet or the Internet.

The computer system 601 can communicate with one or more remote computer systems through the network 630. For instance, the computer system 601 can communicate with a remote computer system of a user (e.g., seizure detection system manager, seizure detection system user, seizure detection data acquirer, seizure detection system scribe, etc). Examples of remote computer systems include servers, personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 601 via the network 630. In some cases, the EEG device module and the seizure detection module will be located within the same computer system. In some cases, the EEG device module will be located within one computer system which is networked to a remote computer system containing the seizure detection module. After performing seizure detection, the remote computer system can then transmit seizure detection results to the computer system containing the EEG device module as well as other remote computer systems that may be used for seizure detection results display. In some cases, different parts of the seizure detection module may be located in different computer systems which have been networked together.

Methods as described herein can be implemented by way of machine (e.g., computer processor) executable code stored on an electronic storage location of the computer system 601, such as, for example, on the memory 610 or electronic storage unit 615. The machine executable or machine readable code can be provided in the form of software. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 601 can include or be in communication with an electronic display 635 that comprises a user interface (UI) 640 for providing, for example, a login screen for an administrator to access software programmed to control the seizure detection system and functionality and/or for providing the operation status health of the seizure detection system. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 605. The algorithm can, for example, be component of software described elsewhere herein and may modulate the seizure detection system parameters (e.g. processing EEG signals, machine learning algorithms, control policy, seizure burden, notifications, etc)

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for seizure detection, comprising:
   (a) receiving a plurality of electroencephalography (EEG) signals over a plurality of channels for a subject;
   (b) preprocessing the plurality of EEG signals by segmenting the plurality of EEG signals for each channel into a plurality of temporal data segments;
   (c) extracting a plurality of features from each temporal data segment for each channel, wherein each temporal data segment is associated with a time epoch;
   (d) applying a machine learning algorithm to the plurality of features to perform a seizure binary classification for each temporal data segment for each channel, thereby generating a plurality of classifications for the plurality of temporal data segments, wherein the seizure binary classification for each temporal data segment comprises classifying each temporal data segment for each channel as (1) seizure-positive or (2) seizure-negative, wherein the plurality of classifications are compared sequentially across a plurality of time epochs on each channel, and a subset of the classifications is discarded if the subset comprises fewer than three seizure-positive classifications in a row;
   (e) aggregating the remaining non-discarded classifications for the plurality of temporal data segments for the plurality of channels over a moving time window;
   (f) determining a seizure burden for the moving time window based on the aggregated classifications, wherein the seizure burden comprises a percentage of the temporal data segments that are classified as seizure-positive, and wherein the seizure burden is a metric that provides a measure of a degree of severity or likelihood of a seizure; and
   (g) generating one or more notifications when the seizure burden is equal to or exceeds one or more thresholds, wherein the one or more notifications are indicative of different seizure activities and are useable for assessing whether the subject is at risk of having a seizure.

2. The method of claim 1, wherein each temporal data segment has a duration ranging from about one second to twenty seconds.

3. The method of claim 2, wherein the duration of each temporal data segment is about ten seconds.

4. The method of claim 1, wherein the moving time window ranges from about one minute to ten minutes.

5. The method of claim 4, wherein the moving time window is about five minutes.

6. The method of claim 1, wherein the one or more notifications are generated in the form of visual, audio, and/or textual alerts.

7. The method of claim 1, wherein a first notification indicative of frequent seizure activity is generated when the seizure burden is equal to or exceeds a first threshold of 10%.

8. The method of claim 1, wherein a second notification indicative of abundant seizure activity is generated when the seizure burden is equal to or exceeds a second threshold of 50%.

9. The method of claim 1, wherein a third notification indicative of continuous seizure activity is generated when the seizure burden is equal to or exceeds a third threshold of 90%.

10. The method of claim 1, wherein the plurality of channels comprises at least three channels.

11. The method of claim 10, wherein the plurality of channels comprises eight channels.

12. The method of claim 1, wherein the plurality of features comprises time and/or frequency domain features that are intrinsic in the plurality of EEG signals.

13. The method of claim 12, wherein the plurality of features comprises at least twenty different time and/or frequency features.

14. The method of claim 12, wherein the plurality of features comprises a plurality of discrete values associated with the time and/or frequency domain features.

15. The method of claim 1, wherein the machine learning algorithm comprises a random forest, a boosted decision tree, a classification tree, a regression tree, a bagging tree, a neural network, or a rotation forest.

16. The method of claim 1, wherein the machine learning algorithm is individually applied to the plurality of features extracted for each channel, such that each channel has a separate iteration of the machine learning algorithm.

17. The method of claim 1, wherein the preprocessing of the plurality of EEG signals further comprises:
   applying a filter to the plurality of EEG signals over the plurality of channels, prior to the segmentation of the plurality of EEG signals.

18. The method of claim 17, wherein the filter comprises a bandpass filter configured to filter the plurality of EEG signals between 1 Hz and 35 Hz.

19. The method of claim 1, further comprising:
   classifying a particular time epoch as associated with a potential electrographic seizure, if the temporal data segments for a subset of the plurality of channels are classified as seizure-positive.

20. The method of claim 19, wherein the subset comprises at least half of the plurality of channels.

21. The method of claim 1, wherein sequential periods of time formed by the time window are non-overlapping.

22. The method of claim 1, further comprising: outputting the seizure burden as a graphical visual element on a display.

23. The method of claim 22, further comprising: displaying the one or more thresholds in the graphical visual element.

24. The method of claim 22, wherein the graphical visual element comprises a time-series plot, bar graph, or chart.

25. The method of claim 24, wherein the time-series plot is configured to change in color as the seizure burden passes a threshold of the one or more thresholds.

26. The method of claim 22, further comprising:
   using the graphical visual element to (i) assess a condition of the subject, (ii) determine a course of treatment, (iii) monitor an effectiveness of a course of treatment if the course of treatment is provided to the subject, or (iv) monitor a progression of the subject's condition over time.

* * * * *